United States Patent [19]

Albrecht et al.

[11] Patent Number: 4,782,065

[45] Date of Patent: Nov. 1, 1988

[54] METHODS AND COMPOSITIONS FOR TREATING VIRAL INFECTIONS

[75] Inventors: Thomas Albrecht; Odd S. Steinsland, both of Galveston, Tex.

[73] Assignee: Board of Regents, The University of Texas System, Austin, Tex.

[21] Appl. No.: 2,981

[22] Filed: Jan. 13, 1987

Related U.S. Application Data

[62] Division of Ser. No. 601,471, Apr. 18, 1984, Pat. No. 4,663,317.

[51] Int. Cl.$^4$ .................. A61K 31/44; A61K 31/47
[52] U.S. Cl. ............................... 514/299; 514/307; 514/934
[58] Field of Search ....................... 514/299, 307

[56] References Cited

U.S. PATENT DOCUMENTS

4,663,317  5/1987  Albrecht et al. ................ 514/211

FOREIGN PATENT DOCUMENTS

0109234  5/1984  European Pat. Off. .
0235931  9/1987  European Pat. Off. .

OTHER PUBLICATIONS

International Search Report.
Albrecht, T. et al. (1984) "Cellular Responses to Human Cytomegalovirus Infection" in CMV; Pathogenesis and Prevention of Human Infection, Birth Defects: Original Article Series, vol. 20, No. 1.
Albrecht, T., Speelman, D. J. and Steinsland, O. S. (1983), Life Sciences, 32:2273.
Albrecht, T., Speelman, D. J., Nokta, M., and Steinsland, O. S. (1984), "Control of Cytomegalovirus Expression and Replication by Modification of the Cellular Response to Virus Infection" (Abstract).
Stanwick, et al. (1977), Infect. Immun. 18:342-347.
Lucas, et al. (1978), J. Exp. Med., 148:940-952.
Robbins, et al. (1980), Virology, 106:317-326.
Miller, et al. (1982), Proc. Natl. Acad. Sci., 79:1629-1633.
Grunberg, et al. (1970), Ann. N.Y. Acad. Sci., 173:122.
Tampieri, et al. (1980), Med. Biol. Environ., 8:199.
Tampiere, et al. (1981), Ann. Sclavo, 23:214.
Yoshikawa, et al. (1984), Jrnl. Virol., 50:489.
Nugent, et al. (1984), Arch. Virol., 81:163.
Dialog Search Report.

Primary Examiner—John Rollins
Attorney, Agent, or Firm—Arnold, White & Durkee

[57] ABSTRACT

The disclosure demonstrates the inhibition of replication of human cytomegalovirus (HCMV) in cultured human embryo skin muscle cells by two separate subclasses of direct-acting smooth muscle relaxing agents. These two subclasses are characterized mechanistically as calcium influx blockers (or calcium channel blockers) and cyclic nucleotide modulators. More specifically, the class of calcium influx blockers is exemplified by the drugs verapamil (and methoxyverapamil), nifedipine (the prototype drug of 1,4 dihydropyridines), and diltiazem. The class of cyclic nucleotide modulators is exemplified by the drugs isobutylmethylxanthine, papaverine (and its synthetic analog dioxyline), forskolin, and sodium nitroprusside. All of these agents inhibit replication of HCMV and HSV.

6 Claims, No Drawings

METHODS AND COMPOSITIONS FOR TREATING VIRAL INFECTIONS

The present application is a Divisional of U.S. Ser. No. 601,471, filed Apr. 18, 1984, U.S. Pat. No. 4,663,317.

BACKGROUND OF THE INVENTION

The present invention relates to methods and compositions for treating viral infections. More specifically, the invention is directed towards the treatment of viral infections through the use of smooth muscle relaxing agents and agents that block the entry of calcium ions ($Ca^{++}$) into cells. These agents appear to act by blocking replication of the target viruses in infected cells.

Advances in the treatment of viral infections have been very slow in coming. Very few efficacious antiviral agents presently exist. A few agents have been touted for their potentially specific antiviral activity are in the research and development stage. The clinical efficacy of these agents, such as interferon and interferon inducers (e.g., polyanionic pyran copolymers and double stranded RNA) have yet to be reproducibly demonstrated.

A few pharmaceutical agents have shown promise in the treatment of isolated viral infections, including the use of amantadine in the treatment of Influenza $A_2$ strains. The use of the antimetabolities, Idoxuridine and Cytarabine, in antiviral therapy is hampered by a narrow spectrum of activity and potentially severe side effects. Methisazone is receiving some support for its use against some pox and vaccinaa strains. Its use in pox infections is generally limited to prophylaxis. In general, there are presently no efficacious antiviral agents that demonstrate a broad spectrum of activity. It now appears that no single broad spectrum agent, or family of agents, may be identified as useful in antiviral treatment. Therefore, research is being directed towards identifying antiviral agents with activity against selected viral diseases.

A novel approach to the treatment of certain viral diseases, including human cytomegalovirus (HCMV), varicella-zoster virus, and herpes simplex virus, is addressed by the present invention. This approach involves the restriction of viral expression and replication in infected cells by controlling and modifying the cellular responses to viral infection.

HCMV causes acute and apparently life-long persistent infections of man (T. H. Weller, N. Eng. J. Med. 285:203-214, 267-274 (1971)). HCMV infection has been determined the causative agent in a number of birth defects, including microencephalopathy, hydroencephalopathy and microthalmia. Other defects associated with pre-natal HCMV infections include severe mental retardation, disordered hepatic function, and hyperbilirubinemia. Although the disease is often asymptomatic in children and adults, HCMV infections in these groups have been shown to result in enlargement of the liver and spleen and deranged erythropoesis. The disease may remain dormant for years, then reactivated by unknown causes. Localized and generalized HCMV infections have been shown to develop after immunosuppressive and anti-neoplastic therapy. HCMV is a member of the herpes family of viruses.

The most widely recognized feature of HCMV-induced cytopathology is the formation of distinct nuclear and cytoplasmic inclusions (CI's) (T. Albrecht, T. Cavello, N. L. Cole, and K. Graves, Lab. Invest., 42:1-7 (1980)). Another HCMV cytopathic effect involves the rounding of fibroblastic cells beginning within the first several hours after infection. By 12-24 hours post-infection, depending on the intensity of the infection, nearly all cells are small and rounded.

The novel approach to restrict virus expression and replication presented by the present invention is to control the cellular response to virus infection. Such approaches may be particularly warranted for human cytomegalovirus since this virus is an important cause of disease for which effective therapeutic agents have not yet been identified. Additionally, as previously noted, HCMV infections present notable changes in cytopathology which suggest that cytopathic-directed therapy might prove particularly efficacious in the treatment of that disease.

SUMMARY OF THE INVENTION

A method is provided for the treatment of human viral diseases, in particular HCMV and HSV, through the use of drugs heretofore unknown to possess antiviral activity. These agents can be classified in a broad sense as direct-acting smooth muscle relaxing agents. Two subclasses of the direct-acting smooth muscle relaxing agents, the calcium influx blockers and cyclic nucleotide modulators, have shown antiviral activity.

DETAILED DESCRIPTION OF THE PREFERRED EMBODIMENT

Inhibition of early cellular responses to HCMV infection is achieved by $Ca^{++}$ influx blockers and other smooth muscle relaxing agents. In response to a number of viral infections, including HCMV, herpes simplex virus (HSV), and varicella-zoster virus, human cells undergo a characteristic sequence of morphologic changes. The sequence of these cellular responses is rounding, "contraction," "relaxation," and enlargement. Rounding of cells begins before 5 hours post-infection (PI) when cells in intermediate stages of rounding are observed, and continues through 12 to 24 hours PI. At this time the population of these rounded cells with the smallest size is similar in diameter to that of the *nucleus* of uninfected cells. By 48 hours PI most infected cells have "relaxed," partially flattened, and begun to enlarge. At later times, HCMV-infected cells are observed to be much enlarged.

The present invention utilizes drugs which inhibit the observed morphologic cascade described above for certain virus-infected cells. The initial response of the cells to infection, cell rounding, is mediated by the activation of contractile elements within the cell. Likewise, cellular control of these contractile elements is mediated by changes in the intracellular concentration of calcium ions. More specifically, numerous cellular responses to early viral infection are consistent with a rise in intracellular free $Ca^{++}$. Thus, these morphologic responses could be related to a change in plasma membrane permeability and a concomitant $Ca^{++}$ influx.

The present invention embodies the realization that certain viral infections may be treated by correcting for these symptomatic changes in cellular morphology. The successful use of smooth muscle-relaxing agents in reversing the cell rounding induced by HCMV is demonstrated by direct microscopic examination of infected cells after drug treatment.

Smooth muscle relaxing agents exert their activity by both indirect (e.g., through modification of smooth muscle nerve transmissions) and direct (i.e., through direct action on the cells) actions. The indirect-acting smooth muscle relaxing agents are represented by a wide variety of agents exhibiting great variations in mechanisms of action. These indirect-acting smooth muscle relaxing agents have not demonstrated activity in inhibiting virus replication in infected cells.

In contrast to the indirect-acting agents, two classes of direct-acting agents, the calcium influx blockers (also referred to as calcium channel blockers) and cyclic nucleotide modulators, as a group demonstrate very high inhibition of viral replication in infected cells.

The calcium influx blockers are represented by three general chemical classes of agents: (1) the 1,4 dihydropyridines (of which the prototype drug is nifedipine), (2) a second class, the verapanoids, which includes verapamil and methoxyverapamil, and (3) a third class characterized by the drug diltiazem.

The smooth muscle relaxing agents that exert their action via modulation of intracellular cyclic nucleotide levels are generally classified as to whether or not they affect the enzyme, phosphodiesterase. Phosphodiesterase is the enzyme responsible for metabolism of cyclic nucleotides. The most effective cyclic nucleotide modulators, in terms of inhibiting viral replication, are represented by the agents isobutylmethylxanthine (IBMX), paperverine, and dioxyline, a synthetic compound that is both chemically and pharmacologically very similar to papaverine. The second class of smooth muscle relaxing cyclic nucleotide modulators exert their activity through poorly understood mechanisms other than through inhibition of phosphodiesterase. This class includes the agents forskolin and sodium nitroprusside.

Although various forms of cytomegaloviruses are known to infect animals, including a pig CMV, mouse CMV, and guinea pig CMV, there is no animal model for human CMV (T. Weller, New England Journal of Medicine 285:203, 267 (1971)). In addition, the animal CMV diseases exhibit numerous distinctive aspects and results obtained for antiviral activity of the above agents for animal CMV's would not be supportive of potential antiviral activity in man. Therefore, for the purposes of the present invention, it was felt that the best evidence available to demonstrate these agents activity in humans was by demonstrating their ability to inhibit viral replication and production in infected human cells in culture.

The cells, human embryo skin muscle cells, are first grown to confluency in Leighton tubes in 1 ml. of Eagle's media supplemented with Earle's salts, 10% fetal calf serum (FCS), and 0.075% sodium bicarbonate. This requires approximately 2-4 days growth. At the end of this time, the tubes contain about $2 \times 10^5$ cells Once confluent, the growth media is removed and 0.3 ml. of the virus stock is placed onto the cells (5 pfu/cell) and allowed to adsorb for 1 hr. at 37° C. The virus stock is aspirated off and the cell monolayer washed twice with maintenance media (Eagle's MEM supplemented with Earle's salts, 5% FCS, and 0.15% sodium bicarbonate). The last wash is replaced with 1 ml. of fresh maintenance media containing the indicated drug concentration. The drug is always made up fresh.

The cells are treated with drug for a total of 120 hours. In some experiments, the drug-containing media is replaced every 24 hrs., and in others, every 48 hrs. This variation has no effect on the results.

To test the level of virus replication during drug treatment, the treated cells are quick-frozen in a Revco −70° C. freezer, then put through two freeze/thaw cycles. The cell-containing tubes are then sonicated in a "bath" sonicator for 45 seconds. The cell lysates are assayed for infectivity by a standard plaque assay. (Albrecht, T. and Weller, T. H. Am. J. Clin. Path. 73:648–651 (1980)). The results of these determinations are shown in the following table:

| Drug | Inhibition of HCMV Replication by Smooth Muscle Relaxing Agents* | | |
|---|---|---|---|
| | Dose (ug/ml) | % Inhibition of Virus Yield | Fold Inhibition |
| Verapamil | 1 | 44.4 | 1.8 |
| | 3 | 27.8 | 1.4 |
| | 10 | 78.3 | 4.6 |
| | 30 | 83.3 | 6.0 |
| Nifedipine | 1 | 34.7 | 1.5 |
| | 3 | 56.1 | 2.3 |
| | 10 | 93.0 | 14.3 |
| | 30 | 99.9 | 1000 |
| Isobutyl-methylxanthine (IBMX) | 30 | 44.0 | 2.27 |
| Papaverine | 1 | 97.2 | 35.7 |
| | 3 | 99.98 | 5000 |
| | 10 | 99.995 | 20000 |
| | 30 | 99.998 | 50000 |
| Forskolin | 1 | 40.9 | 1.7 |
| | 3 | 54.5 | 2.2 |
| | 10 | 88.2 | 8.5 |
| Sodium Nitroprusside | 1 | 45.5 | 1.8 |
| | 3 | 45.5 | 1.8 |
| | 10 | 60.0 | 2.5 |
| | 30 | 99.3 | 143 |

*multiplicity of infection = 5 pfu/cell

Further tests of the smooth muscle relaxing agents against two types of herpes simplex virus (HSV-1 and HSV-2) demonstrate the usefulness of the present invention in inhibiting the replication of herpes virus. The particular strain of HSV-1 utilized was KOS and HSV-2 was 198. The activity of the agents against HSV was determined in the same manner as described above for CMV. Both of the viral strains were grown in human embryo skin muscle cells in culture and the infected cells then transferred to media containing 30 ug/ml of the indicated agent and the PFU determined at 24 hours PI. These results are compiled in the following table.

| | Inhibition of HSV-1 and HSV-2 by Smooth Muscle Relaxing Agents* | |
|---|---|---|
| Yield | % Inhibition of Virus | |
| Drug | HSV-1 | HSV-2 |
| Verapamil | 96.1 | 95.8 |
| Papaverine | 86.1 | 67.7 |
| Sodium Nitroprusside | 0 | 53.8 |

*multiplicity of infection = 5 pfu/cell

The finding that direct-acting smooth muscle relaxing agents are active in treating virus-infected human tissue culture cells suggest that such agents will prove useful in treating viral infections in man. The agents do not undergo appreciable entero-hepatic metabolism prior to distribution throughout the body, nor do they require metabolism for "activation." Likewise, these viral diseases present similar morphologic changes in infected cells both in vivo and in vitro. For many years, it has been shown that in vitro antiviral activity typically correlates with in vivo activity. In contrast, the main problem has often been the finding of untoward reactions (toxicities) in vivo that were not seen in vitro.

Since the present agents are in clinical use, this will not be a problem. Therefore, it is expected that these agents can be administered to an infected patient by all routes presently indicated for their use. It is further expected that topical preparations will be active in treating lesions associated with viral infection of this sort.

The instant invention has been disclosed in connection with standard laboratory procedures used by the applicant. However, it will be apparent to those skilled in the art that variations may be undertaken without departing from the spirit and scope of the invention. More specifically, it will be apparent that certain agents that are both chemically and pharmacologically related may be sutstituted to achieve the observed antiviral effect. For example, methoxyverpamil and verapamil are virtually indistinguishable pharmacologically as are papaverine and dioxyline and would be expected to give similar results. These and similar substitutes will be apparent to those skilled in the art and are within the spirit and scope of the invention.

What is claimed is:

1. A method for treating cytomegalovirus infections in an infected human host comprising administering an effective amount of papaverine or dioxyline to the infected human host.

2. The method of claim 1 wherein the administered agent is papaverine.

3. The method of claim 1 wherein the administered agent is dioxyline.

4. A method for inhibiting cytomegalovirus replication in an infected human host comprising administering an effective amount of papaverine or dioxyline to the infected human host.

5. The method of claim 4 wheren the administered agent is papaverine.

6. The method of claim 4 wherein the administered agent is dioxyline.

* * * * *